(12) United States Patent
Hajianpour

(10) Patent No.: US 7,060,029 B1
(45) Date of Patent: Jun. 13, 2006

(54) SPECULUM WITH ATTACHABLE BLADES FOR LATERAL WALL RETRACTION

(75) Inventor: Zoya Hajianpour, Fort Lauderdale, FL (US)

(73) Assignee: Zoya, Inc., Sunrise, FL (US)

( * ) Notice: Subject to any disclaimer, the term of this patent is extended or adjusted under 35 U.S.C. 154(b) by 131 days.

(21) Appl. No.: 10/823,910

(22) Filed: Apr. 14, 2004

(51) Int. Cl.
   *A61B 1/267* (2006.01)
(52) U.S. Cl. .................. 600/190; 600/184; 600/196
(58) Field of Classification Search ........... 600/184, 600/190, 196, 201, 210, 214, 215, 219, 220, 600/222, 235
See application file for complete search history.

(56) References Cited

U.S. PATENT DOCUMENTS

| | | | |
|---|---|---|---|
| 4,130,113 A | 12/1978 | Graham | |
| 4,994,070 A | 2/1991 | Waters | |
| 5,377,667 A * | 1/1995 | Patton et al. | 600/184 |
| 5,400,774 A | 3/1995 | Villalta et al. | |
| 5,509,893 A | 4/1996 | Pracas | |
| 6,024,697 A | 2/2000 | Pisarik | |
| 6,036,638 A * | 3/2000 | Nwawka | 600/186 |
| 6,048,308 A * | 4/2000 | Strong | 600/205 |
| 6,280,379 B1 * | 8/2001 | Resnick | 600/220 |
| 6,364,832 B1 * | 4/2002 | Propp | 600/220 |
| 6,394,950 B1 * | 5/2002 | Weiss | 600/205 |
| 6,416,467 B1 * | 7/2002 | McMillin et al. | 600/224 |
| 6,428,474 B1 * | 8/2002 | Weiss | 600/224 |
| 6,432,048 B1 | 8/2002 | Francois | |
| 6,436,033 B1 | 8/2002 | Tan | |
| 6,527,710 B1 | 3/2003 | Davidson et al. | |
| 6,569,091 B1 | 5/2003 | Diokno et al. | |

FOREIGN PATENT DOCUMENTS

WO    WO 98/33431    8/1998

* cited by examiner

*Primary Examiner*—Beverly M. Flanagan
(74) *Attorney, Agent, or Firm*—Ronald V. Davidge

(57) ABSTRACT

A pair of lateral structures is removably attached to a vaginal speculum after the speculum is inserted and opened to retract anterior and posterior vaginal tissue. Each of the lateral structures includes a blade extending along a side of a space provided between the opposed blades of the vaginal speculum to retract lateral vaginal tissue.

20 Claims, 1 Drawing Sheet

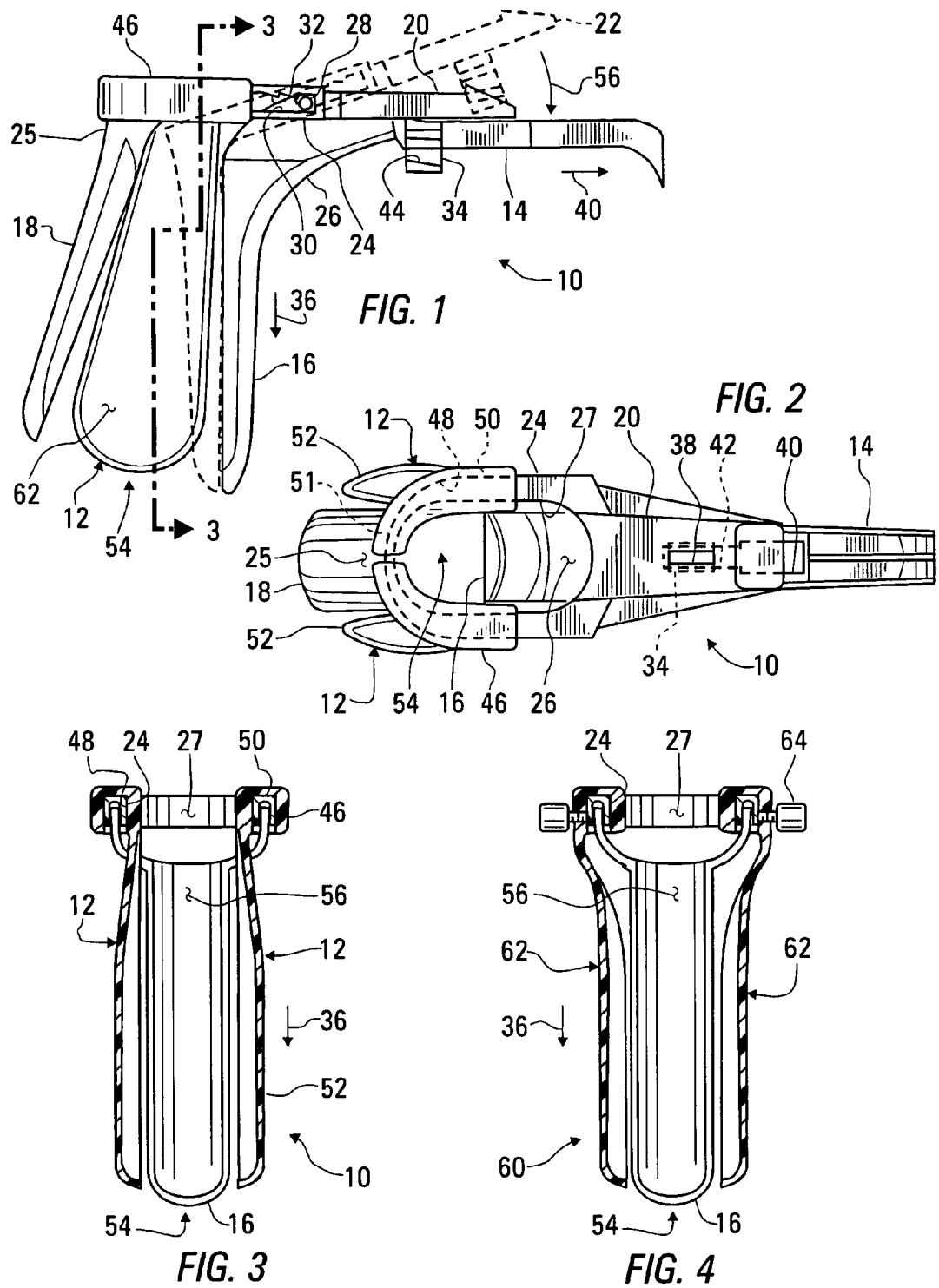

SPECULUM WITH ATTACHABLE BLADES FOR LATERAL WALL RETRACTION

BACKGROUND OF THE INVENTION

1. Field of the Invention

This invention relates to a vaginal speculum and, more particularly, to a vaginal speculum including means providing for retraction of the lateral walls of the vagina.

2. Summary of the Background Art

A vaginal speculum is an important medical tool for providing visual access to structures within the vaginal opening, including the cervix, during a gynecological examination. A conventional vaginal speculum includes a pair of opposed blades movable between a closed position, with the opposed blades lying against one another, and an open position, with the opposed blades spaced apart from one another. During a gynecological examination, the blades of the speculum are inserted into the vagina with the opposed blades in the closed position. Then opposed blades are then opened, allowing the vagina to be visualized through an opening in a frame disposed adjacent a proximal end of the blades. Typically, the speculum additionally includes latching or screw means to hold the movable blade in its open position, or in additional positions between its closed and fully open positions.

When the conventional speculum is thus inserted and opened, its blades press upon the anterior and posterior walls of the vagina. However, since the blades do not extend along the lateral walls of the vagina, in certain patients, these lateral walls collapse inward, blocking visual examination of the vagina and cervix as required during a gynecological examination. This problem is often encountered in patients who have had multiple vaginal deliveries of babies and in obese patients. The levator and musculature of a patient who has experienced multiple vaginal deliveries may be relaxed so that the lateral vaginal walls collapse inward during the examination, with the muscles having been mechanically overstressed from the multiple deliveries and from weight gain associated with multiple pregnancies. An obese patient may present a similar problem during examination due to excessive connective tissue beneath the pelvic peritoneum. One effect of this problem is that the clinician may extend the blades of the speculum farther than otherwise necessary in an attempt to pull sagging tissue into a stretched condition, resulting in additional patient discomfort.

This problem may be alleviated by providing the speculum with an elastic sheet or membrane extending between the blades in their open position to hold the lateral vaginal wall tissue in place. For example, International Application WO 98/33431 describes the use of a sleeve of elastic material, placed over the blades or jaws of the speculum to stretch when the jaws are opened so that sleeve portions span openings between the jaws, preventing the prolapse of tissue into these openings. The sleeve can be supplied in a rolled condition for ease of application, and may have a bead at one end to assist in its removal from the speculum jaws. Alternately, as described in U.S. Pat. No. 6,432,048, loose vaginal tissue may be retained in a lateral direction by a speculum including a flexible membrane structure, such as a pair of membranes that extend between the blades. The membranes are configured to remain in a generally collapsed configuration when the blades are in the closed position to avoid interfering with insertion or withdrawal of the speculum. What is needed is a speculum having rigid surfaces for holding the prolapsed lateral tissue in place, since such surfaces do not rely on the forces necessary to stretch membranes or elastic materials sufficiently for such purposes.

Alternately, lateral vaginal sidewall tissue may be held in place with a device that expands laterally, such as the vaginal speculum described in U.S. Pat. No. 4,994,070, which has a sheet member of inherently resistant material capable of being rolled into a normal position in which the member forms a narrow, generally elongate shape. The sheet member is expandable under its inherent resilience to a dilated position in which the member forms a hollow generally open ended shape having a substantially continuous sidewall. The sheet member is provided with first and second handle members that are attached to the sheet member along left and right edges, respectively. Again, what is needed is a speculum having rigid surfaces for holding the prolapsed tissue in place, since such rigid surfaces can be shaped optimally for this purpose.

As described in U.S. Pat. No. 6,527,710, the lateral walls of the vagina may alternately be supported by a number of rounded ribs, extending parallel to one another between a stationary blade and a link fashioned as a moving blade of a speculum. Each of the ribs is pivotally attached at one end to the stationary blade and at the other end to the link. When the speculum is closed, the ribs and the link lie against the stationary blade. As the speculum is opened, the ribs pivot away from the surface of the stationary blade with the link. What is needed is a speculum having rigid surfaces for holding the prolapsed tissue in place without multiple twisting movements, which may cause patient discomfort.

U.S. Pat. Nos. 5,509,893 and 6,436,033 describe vaginal specula having four blades, comprising two pairs of blades that open in directions perpendicular to one another. While two of these blades would support sagging lateral vaginal tissue, the closed state of the speculum presents a cylindrical blade structure. What is needed is a speculum having insertable lateral blades, so that the speculum can be inserted into the vagina in a flattened condition, presenting a minimum cross sectional area for ease of insertion and minimum patient discomfort.

U.S. Pat. No. 6,569,091 describes a vaginal speculum consisting of two pivotally interconnected and disconnectable jaws, each of which supports a blade assembly movable in a longitudinal direction. Additionally, one of the blades can be moved circumferentially. Each blade can be completely withdrawn from the speculum, even during the procedure. Circumferential displacement of one of the blades in both directions makes it possible to observe the vaginal cavity over the entire periphery without rotating the entire speculum or replacing it with another tool. However, to permit such circumferential movement, both the blade and the jaw on which it is mounted are arcuate in shape, with the jaws being shown as coming together to form a cylinder split into halves along its axis. What is needed is a speculum including connectable blades for retaining prolapsed tissue without placing such requirements on the shape of the speculum in it closed condition, in which it is inserted into the vagina.

SUMMARY OF THE INVENTION

According to a first aspect of the invention, apparatus is provided for retracting wall surfaces within a vagina during examination with a speculum having opposed blades opened for retracting tissue from anterior and posterior wall surfaces of the vagina and a frame having an opening through which internal structures are visualized. The apparatus includes a first lateral structure having a first handle portion and a first lateral blade. The first handle portion includes a downwardly open slot for removably attaching the first lateral structure to a first side of the frame of the speculum. The first lateral blade extends downward from the first handle portion, laterally adjacent a space between the opened opposed blades of the speculum, with the first side of the frame engaged within the downwardly open slot of the first handle portion.

The apparatus preferably additionally includes a second lateral structure having a second handle portion and a second lateral blade. The second handle portion includes a downwardly open slot for removably attaching the second lateral structure to a second side of the frame of the speculum. The second lateral blade extends downward from the second handle portion, laterally adjacent a space between the opened opposed blades of the speculum, with the second side of the frame engaged within the downwardly open slot of the second handle portion.

According to another aspect of the invention, a method is provided for performing a vaginal examination. The method includes: inserting an opposed pair of blades of a speculum into a vaginal opening with the opposed blades lying against one another; opening the opposed pair of blades to expose internal structures within the vaginal opening through a space between the opposed pair of blades; after opening the opposed pair of blades, inserting a first lateral blade within the vaginal opening to extend along a first side of the space between the opposed pair of blades; attaching a handle portion disposed at a proximal end of the first lateral blade to a first side of an open frame of the speculum, extending adjacent a proximal end of the space between the opposed pair of blades; removing the handle portion of the first lateral structure from the frame of the speculum; withdrawing the first lateral blade from the vaginal opening; closing the opposed pair of blades within the vaginal opening to lie against one another; and removing the opposed pair of blades from the vaginal opening.

BRIEF DESCRIPTION OF THE FIGURES

FIG. 1 is a left elevation of a speculum built in accordance with the invention;

FIG. 2 is a plan view of the speculum of FIG. 1;

FIG. 3 is a cross-sectional view of the speculum of FIG. 1, taken as indicated by section lines 3—3 therein; and FIG. 4 is a cross-sectional view of an alternative version of a speculum built in accordance with the invention, taken as the cross-sectional view of FIG. 3.

DETAILED DESCRIPTION OF THE INVENTION

FIG. 1 is a left elevation of a speculum 10 built in accordance with the invention to include a pair of detachable lateral sections 12 for holding prolapsed vaginal tissue in place after the speculum 10 is inserted and opened. Various other aspects of the speculum 10 may be conventional. For example, the speculum 10 includes a handle 14, a stationary blade 16 attached to descend from the handle 14, and a movable blade 18 attached to a lever 20, being slidably and pivotally attached to the handle. The movable blade 18 and lever 20 are shown in solid lines with the speculum fully open and in dashed lines 22 with the speculum fully closed. In the fully closed position, the movable blade 18 lies against the stationary blade 16, presenting a minimally sized structure for insertion into the vagina. Thus, the stationary blade 16 and the movable blade 18 together form a pair of opposed blades 16, 18, movable between a closed position and an open position.

FIG. 2 is a plan view of the speculum 10, shown in a fully open position with the lateral sections 12 attached thereto. The movable blade 18 is seen to be attached to the lever 20 by means of a frame 24, extending from a proximal end 25 of the movable blade 18 upwardly adjacent a proximal end 26 of the stationary blade 16. The frame 24 includes an opening 27 through which the structure of the vagina and cervix are visualized with the blades 16, 18 inserted and separated by opening.

The movable blade 18 is pivotally attached to the lever 20 by means of a pair of pins 28 extending outward within slots 30 in the frame 24. The slots 30 include a stepped surface 32 providing several locations at which the movable blade 18 may be pivoted on the handle 14. The angle of attachment between the movable blade 18 and the handle 14 is further determined by a slotted tabs 34 extending downward, in the direction of arrow 36, from opposite sides of a slot 38 within the lever 20. When the lever 20 is slid fully in the direction of arrow 40 to close the speculum 10, the slotted tabs 34 can be freely moved within an enlarged opening 40 within the handle 14. As the lever 20 is slid opposite the direction of arrow 20 to open the speculum 10, the sides of a narrowed slot 42 within the handle engage slots 44 within the slotted tabs 34, preventing rotation of the lever 20 about the pins 28 while permitting sliding movement.

FIG. 3 is a cross-sectional view of the speculum 10, taken as indicated by section lines 3—3 in FIG. 1, to particularly show how the lateral sections 12 are removably attached to the frame 24. Each of the lateral sections 12 includes a curved handle portion 46 having a downwardly open J-shaped slot 48 fitting over a straight lateral portion 50 of the frame 24 and additionally extending inwardly over part of a curved end portion 51 of the frame 24. Each of the lateral sections 12 also includes a lateral blade portion 52 extending downward outwardly adjacent a space 54 between the stationary blade 16 and the moving blade 18 with the speculum 10 fully open. Thus, each of the curved handle portions 46 is disposed at a proximal end 55 of the associated lateral blade portion 52.

According to one version of the invention, the stationary blade 16 and the movable blade 18 are first inserted into the vagina with the speculum 10 in the closed position, so that these blades 16, 18 are held together as indicated by the dashed lines 22, presenting a minimum cross-section for easiest insertion, and with the lateral sections 12 disconnected from the speculum 10. Then, the lever 20 is pivoted in the direction of arrow 56, being moved into place against the handle portion 14. Next, the lever 20 is slid opposite the direction of arrow 40, bringing the movable blade 18 into the fully open position indicated by dashed lines 22. Next, the curved blade portion 52 of each of the lateral sections 12 is individually inserted into the vagina, being held by the corresponding handle portion 46, and being manipulated to push sagging tissue from a corresponding lateral vaginal wall outward. This insertion movement moves the downwardly open J-shaped slot 48 within each of the handle portions 46 into engagement with a corresponding portion 50 of the frame 24, with this engagement subsequently holding the lateral section 12 in place.

When the lateral sections 12 have been installed in this way, each of the lateral sections 12 extends downward through the opening 27. Since the opening 12 diminishes as the speculum 10 is closed, with the opening 12 moving in the direction of arrow 40 into place mostly over the curved upper portion 56 of the stationary blade 16, it is necessary to remove the lateral sections 12 before the speculum 10 is fully closed. Thus, after the examination has been completed, the lateral sections 12 are disengaged from the frame 24 and removed from the speculum 10 and from the vagina. Then, the speculum is closed and withdrawn from the vagina.

FIG. 4 is a cross-sectional view of an alternative version 60 of a speculum built in accordance with the invention, including a pair of lateral sections 62 extending downward outside the frame 24 instead of inside the opening 27 within the frame 24. The cross-section of FIG. 4 is taken in the manner of the cross-section of FIG. 3. The lateral sections 62 are additionally shown as being held in place by a pair of clamping screws 64. Other aspects of the alternative version 60 are as explained above for the speculum 10 in FIGS. 1–3, with like reference numbers being accorded.

While the alternative version 60 is preferably inserted within the vagina as described above, the lateral sections 62 need not be removed before the alternative version 60 is closed. Thus, the lateral sections 62 can be removed separately after the alternative version 60 is closed. This version of the process of using the alternative version 60 has the advantage of preventing the pinching of sagging lateral vaginal tissue between the stationary blade 16 and the moving blade, thereby eliminating a potential cause for patient discomfort. However, the version of FIG. 3 has an advantage of relatively easy insertion of the curved blade portions 52 within the vagina.

While both the specula 10, 60 are shown generally as being composed of an opaque thermoplastic resin, it is understood that the such devices, and portions thereof, such as the lateral sections 12, 62 can readily be composed of transparent thermoplastic materials to aid in the visualization of certain areas. It is further understood that such devices and portions thereof may be composed of metal for greater strength and stiffness. Metal versions of specula, to which lateral sections may be applied in the manner of the invention, are known to have clamping screws providing for fine adjustments in the sliding and pivoting motions of the movable blade relative to the handle and stationary blade. The thumbscrews 64 may be optionally applied to the version of the lateral sections 12 otherwise shown in FIG. 3.

The lateral sections 12, 62 may be packaged and sold separately from the remaining portions of a speculum, or these parts may be packaged and sold together. Two or more variations of lateral sections 12, 62 may be sold for use with a single version of a speculum, with the different versions of the lateral sections 12, 64 being optimized for use at different degrees in which the speculum is opened for different procedures and different patients.

While the invention has been described and shown in its preferred versions or embodiments, it is understood that this description has been given only by way of example, and that many variations in the arrangement of parts may be made without departing from the spirit and scope of the invention, as described in the appended claims.

What is claimed is:

1. Apparatus for retracting wall surfaces within a vagina during examination with a speculum having opposed blades opened for retracting tissue from anterior and posterior wall surfaces of the vagina and a frame having an opening through which internal structures are visualized, wherein the apparatus comprises a first lateral structure including:

a first handle portion including a J-shaped downwardly open slot extending along a first lateral portion of the frame and inwardly along a first curved portion of the frame with the first side of the frame engaged within the downwardly open slot for removably attaching the first lateral structure to a first side of the frame of the speculum; and a first lateral blade extending downward from the first handle portion, laterally adjacent a space between the opened opposed blades of the speculum with the first side of the frame engaged within the downwardly open slot of the first handle portion.

2. The apparatus of claim 1, additionally including a clamping screw for holding the handle portion on the frame with the frame extending through the downwardly open slot.

3. The apparatus of claim 1, wherein the first lateral blade extends downward inwardly adjacent the downwardly open slot.

4. The apparatus of claim 1, wherein the first lateral blade extends downward outwardly adjacent the downwardly open slot.

5. The apparatus of claim 1, wherein the apparatus additionally comprises a second lateral structure including:

a second handle portion including a J-shaped downwardly open slot extending along a second lateral portion of the frame and inwardly along a second curved portion of the frame with a second side of the frame engaged within the downwardly open slot for removably attaching the second lateral structure to a second side of the frame of the speculum, the second side of the speculum being opposite the first side of the speculum; and a second blade extending downward from the second handle portion, laterally adjacent the space between the opened opposed blades of the speculum with the second side of the frame engaged within the downwardly open slot of the second handle portion.

6. A vaginal speculum comprising:

a pair of opposed blades movable between a closed position and an open position, wherein the opposed blades lie together in the closed position for insertion into a vagina, and wherein the opposed blades are separated from one another for retracting vaginal tissue in the open position;

a frame disposed adjacent a proximal end of the pair of opposed blades, wherein the frame includes an opening for visualizing internal structures within the vagina through a space extending between the opposed blades in the open position;

a first lateral structure including a first handle portion at a proximal end of the first lateral structure and a first lateral blade, wherein the first handle portion includes a downwardly open slot removably attaching the first lateral structure to a first side of the frame, and wherein the first lateral blade extends downward from the first handle portion, adjacent a fist side of the space extending between the opposed blades in the open position when the first lateral structure is attached to the first side of the frame; and a second lateral structure including a second handle portion at a proximal end of the second lateral structure and a second lateral blade, wherein the second handle portion includes a downwardly open slot removably attaching the second lateral structure to a second side of the frame, opposite the first side of the frame, wherein the second lateral blade extends downward from the second handle portion, laterally adjacent a second side of the space extending between the opposed blades in the open position, opposite the first side of the space extending between opposed blades in the open position, when the second lateral structure is attached to the second side of the frame, and wherein the first and second lateral structures are separately attached to separate portions of the frame.

7. A vaginal speculum comprising:
a pair of opposed blades movable between a closed position and an open position, wherein the opposed blades lie together in the closed position for insertion into a vagina, and wherein the opposed blades are separated from one another for retracting vaginal tissue in the open position;
a frame, including a curved end portion and a straight lateral portion extending along each side, disposed adjacent a proximal end of the pair of opposed blades, wherein the frame includes an opening for visualizing internal structures within the vagina through a space extending between the opposed blades in the open position;
a first lateral structure including a first handle portion at a proximal end of the first lateral structure and a first lateral blade, wherein the first handle portion includes a downwardly open slot for removably attaching the first lateral structure to a first side of the frame, and wherein the first lateral blade extends downward from the first handle portion, adjacent a fist side of the space extending between the opposed blades in the open position when the first lateral structure is attached to the first side of the frame; and
a second lateral structure including a second handle portion at a proximal end of the second lateral structure and a second lateral blade, wherein the second handle portion includes a downwardly open slot for removably attaching the second lateral structure to a second side of the frame, opposite the first side of the frame, and wherein the second lateral blade extends downward from the second handle portion, laterally adjacent a second side of the space extending between the opposed blades in the open position, opposite the first side of the speace extending between opposed blades in the open position, when the second lateral structure is attached to the second side of the frame,
wherein each of the downwardly open slots is a J-shaped slot extending along one of the lateral portions of the frame and inwardly along of the curved end portion of the frame with the first and second lateral structures attached to the frame.

8. The vaginal speculum of claim 7, wherein the first lateral structure and the second lateral structure each additionally include a clamping screw engaging the frame with the lateral structures attached to the frame.

9. The vaginal speculum of claim 7, wherein the first lateral blade and the second lateral blade extend downward through the opening within the frame with the lateral structures attached to the frame.

10. The vaginal speculum of claim 7, wherein the first lateral blade and the second lateral blade extend downward outwardly from the frame with the lateral structures attached to the frame.

11. A method for performing a vaginal examination, comprising:
inserting an opposed pair of blades of a speculum into a vaginal opening with the opposed blades lying against one another;
opening the opposed pair of blades to expose internal structures within the vaginal opening through a space between the opposed pair of blades;
after opening the opposed pair of blades, inserting a first lateral blade within the vaginal opening to extend along a first side of the space between the opposed pair of blades;
attaching a handle portion disposed at a proximal end of the first lateral blade to a first side of an open frame of the speculum, extending adjacent a proximal end of the space between the opposed pair of blades;
removing the handle portion of the first lateral structure from the frame of the speculum;
withdrawing the first lateral blade from the vaginal opening;
closing the opposed pair of blades within the vaginal opening to lie against one another; and
removing the opposed pair of blades from the vaginal opening.

12. The method of claim 11, additionally comprising:
after opening the opposed pair of blades, inserting a second lateral blade within the vaginal opening to extend along a second side of the space between the opposed pair of blades, opposite the first side of the space between the opposed pair of blades;
attaching a handle portion disposed at a proximal end of the second lateral blade to a second side of an open frame of the speculum, extending adjacent a proximal end of the space between the opposed pair of blades;
removing the handle portion of the second lateral structure from the frame of the speculum; and
withdrawing the second lateral blade from the vaginal opening.

13. The method of claim 12, wherein
the lateral blades are inserted through an opening within the open frame, and
the lateral blades are removed from the vaginal opening before the opposed pair of blades are closed.

14. The method of claim 12, wherein
the lateral blades are inserted outwardly adjacent opposite sides of the open frame, and
the opposed pair of blades are closed before the lateral blades are removed from the vaginal opening.

15. The method of claim 12, wherein
each of the handle portions disposed at a proximal end of a lateral blade includes a slot open adjacent the lateral blade, and
each of the handle portions is attached to the open frame with a portion of the open frame extending within the slot.

16. A method for performing a vaginal examination, comprising:
inserting an opposed pair of blades of a speculum into a vaginal opening with the opposed blades lying against one another;
opening the opposed pair of blades to expose internal structures within the vaginal opening through a space between the opposed pair of blades;
after opening the opposed pair of blades, inserting a first lateral blade within the vaginal opening to extend along a first side of the space between the opposed pair of blades;
after opening the opposed pair of blades, inserting a second lateral blade within the vaginal opening to extend along a second side of the space between the opposed pair of blades, opposite the first side of the space between the opposed pair of blades;
attaching a first handle portion, disposed at a proximal end of the first lateral blade, including a slot open adjacent the first lateral blade, to a first side of an open frame of the speculum, wherein the open frame includes a curved end portion and a straight lateral portion extending along each side, wherein the slot within the first handle portion is J-shaped to extend along a first one of the straight lateral portions and inward along the curved end portion of the open frame, and wherein the first handle portion is attached to extend adjacent a proximal end of the space between the opposed pair of blades;

attaching a second handle portion, disposed at a proximal end of the second lateral blade, including a slot open adjacent the second lateral blade, to a second side of an open frame of the speculum, wherein the slot within the second handle portion is J-shaped to extend along a second one of the straight lateral portions and inward along the curved end portion of the open frame, and wherein the second handle portion is attached to extend adjacent a proximal end of the space between the opposed pair of blades;

removing the handle portion of the first lateral structure from the frame of the speculum;

removing the handle portion of the second lateral structure from the frame of the speculum;

withdrawing the first lateral blade from the vaginal opening;

withdrawing the second lateral blade from the vaginal opening;

closing the opposed pair of blades within the vaginal opening to lie against one another; and removing the opposed pair of blades from the vaginal opening.

17. The method of claim 12, wherein each of the handle portions is attached to the open frame by tightening a clamping screw against the open frame; and each of the clamping screws is loosened before removing the handle portion from the open frame.

18. The method of claim 16, wherein the lateral blades are inserted through an opening within the open frame, and the lateral blades are removed from the vaginal opening before the opposed pair of blades are closed.

19. The method of claim 16, wherein the lateral blades are inserted outwardly adjacent opposite sides of the open frame, and the opposed pair of blades are closed before the lateral blades are removed from the vaginal opening.

20. The method of claim 16, wherein each of the handle portions is attached to the open frame by tightening a clamping screw against the open frame; and each of the clamping screws is loosened before removing the handle portion from the open frame.

* * * * *